United States Patent
Crawford et al.

(10) Patent No.: US 6,902,534 B2
(45) Date of Patent: Jun. 7, 2005

(54) METHOD AND KIT OF COMPONENTS FOR DELIVERING BLOOD TO A PORTABLE CLINICAL ANALYZER

(75) Inventors: Jamieson William Maclean Crawford, New York, NY (US); Frank Francavilla, Newton, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 312 days.

(21) Appl. No.: 10/106,149

(22) Filed: Mar. 25, 2002

(65) Prior Publication Data

US 2002/0143272 A1 Oct. 3, 2002

Related U.S. Application Data (60) Provisional application No. 60/280,444, filed on Mar. 30, 2001, provisional application No. 60/280,437, filed on Mar. 30, 2001, and provisional application No. 60/280,403, filed on Mar. 30, 2001.

(51) Int. Cl.[7] ............................. A61B 5/00; B65D 81/00
(52) U.S. Cl. ...................................................... 600/573
(58) Field of Search ................................. 600/573, 576, 600/578, 584; 604/272, 158, 274, 161, 164.01, 164.07, 168.01, 170.02; 606/167, 186

(56) References Cited

U.S. PATENT DOCUMENTS

| | | | |
|---|---|---|---|
| 3,640,267 A | 2/1972 | Hurtig et al. | |
| 5,080,865 A | 1/1992 | Leiner et al. | |
| 5,096,669 A | 3/1992 | Lauks et al. | |
| 5,449,351 A | * 9/1995 | Zohmann | ...................... 604/272 |
| 5,470,319 A | 11/1995 | Mayer | |
| 5,638,828 A | 6/1997 | Lauks et al. | |
| 5,653,243 A | 8/1997 | Lauks et al. | |
| 5,666,967 A | 9/1997 | Lauks et al. | |
| 5,779,650 A | 7/1998 | Lauks et al. | |
| 5,849,505 A | * 12/1998 | Guirguis | ...................... 435/7.2 |
| 6,010,463 A | 1/2000 | Lauks et al. | |
| 6,350,254 B1 | 2/2002 | Wilkinson et al. | |
| 6,558,353 B2 | * 5/2003 | Zohmann | ...................... 604/158 |

FOREIGN PATENT DOCUMENTS

EP   0 396 016   4/1990

* cited by examiner

*Primary Examiner*—Max F. Hindenburg
*Assistant Examiner*—Brian Szmal (57) ABSTRACT

A kit and a method are provided for facilitating point-of-care testing of bodily fluid. The kit includes a point-of-care testing cartridge and a plastic fitting for use with a syringe to deliver the fluid sample to the testing cartridge. In other embodiments, the kit includes a plastic cannula in place of a fitting. The syringe and plastic cannula can be used with an IV access kit to obtain a sample of fluid. The syringe and plastic cannula then can be used to deliver the fluid to the reservoir the testing cartridge.

10 Claims, 11 Drawing Sheets

METHOD AND KIT OF COMPONENTS FOR DELIVERING BLOOD TO A PORTABLE CLINICAL ANALYZER

RELATED APPLICATIONS

This application claims priority on U.S. Provisional Patent Appl. No. 60/280,403, U.S. Provisional Patent Appl. No. 60/280,437 and U.S. Provisional Patent Application No. 60/280,444, all of which were filed on Mar. 30, 2001.

BACKGROUND OF THE INVENTION

1. Field of the Invention

The subject invention relates to a method of using a syringe to draw a sample of fluid and to deliver the fluid to a point-of-care testing cartridge. The subject invention also relates to a kit of parts that can be used with a portable clinical analyzer for point-of-care clinical analysis of a sample of fluid drawn from a patient.

2. Description of the Related Art

Many medical procedures require diagnostic tests to be performed on a sample of a patient's fluid. Fluid often is collected from a patient by employing a needle holder assembly and one or more evacuated tubes. The tubes are labeled carefully and shipped to a laboratory for analysis. The results of the laboratory analysis then are reported back to the health care provider. The results, of course, could be rushed in emergency situations, but absent an emergency would require more then one day between the time the sample is drawn from the patient to the time that the laboratory analysis is reported to the health care provider.

Devices have been developed for performing at least certain diagnostic tests on a sample of fluid at the point-of-care. The point-of-care diagnostic equipment includes a syringe for receiving a sample of fluid from a patient, a small disposable testing cartridge for receiving a portion of the fluid from the syringe and a portable clinical analyzer for analyzing the fluid and outputting the results. Combinations of testing cartridges and portable clinical analyzers are marketed in the United States by i-STAT Corporation, AVL Scientific Corporation and Diametrics Medical, Inc. The systems produced by these and other companies share certain common features. In particular, the testing cartridge of each system typically has a small rectangular housing about 1"×2" and about 0.25" thick. The housing includes an internal reservoir with a volume of between about 65 $\mu$l and 110 $\mu$l. An inlet port extends through an external wall of the testing cartridge and communicates with the internal reservoir. The cartridge further includes contact pads and sensors that can be placed in communication with the portable clinical analyzer. An example of an i-STAT point-of-care testing cartridge is shown in U.S. Pat. No. 5,638,828.

The prior art point-of-care testing systems are employed with a syringe to draw a sample of fluid from a patient. The syringe then is used to eject a portion of the fluid sample into the inlet port of the point-of-care testing cartridge. The inlet port of the cartridge then is closed and the cartridge is placed in communication with the portable clinical analyzer for performing certain specified diagnostic tests on the sample of fluid in the cartridge. The analyzer then provides a very quick output of the test results without the need for sending the fluid sample to the laboratory.

Point-of-care testing systems provide several efficiencies over systems that require virtually all diagnostic tests to be performed at a location remote from the point-of-care. The small size of the testing cartridge facilitates storage and shipment of the cartridges while also contributing to the portability of the system. However, with regards to transferring a collected sample to the cartridge, the small cartridges can be very difficult to use. For example, alignment of the distal end of the syringe with the inlet port of the testing cartridge can be complicated and difficult. A misalignment or imprecise mating of the syringe with the inlet port of the testing cartridge can lead to a loss of a portion of the collected fluid sample. Fluid that is not delivered efficiently from the syringe into the inlet port of the testing cartridge create the potential for disease transmission. Similarly, a loss of fluid during the transfer from the syringe to the testing cartridge can leave an insufficient volume of fluid for performing the required diagnostic tests. An insufficient volume of fluid to perform the required tests can require the health care worker to return to the patient for a second sample of fluid. This is time consuming for the health care worker and traumatic for the patient. Additionally, some testing cartridges may require an insufficiently filled cartridge to be discarded and a new cartridge to be employed with the new sample of fluid. Thus, inefficiencies in the transfer of fluid from the syringe to the testing cartridge can generate excess costs for additional testing cartridges.

IV access systems of tubes and fittings often are used for delivering liquid solutions to a patient. One such fitting is a blunt plastic tube with opposed proximal and distal ends and a lumen extending therebetween. Portions of the lumen adjacent the proximal end of the plastic fitting define a large tapered opening dimensioned to achieve a fluid-tight engagement with the tapered tip of a fitting, such as the tip at the distal end of a syringe. The proximal end of the plastic fitting includes a pair of diametrically opposite lugs that are configured for engagement with the internal threads on a collar. Threaded engagement of the lugs on the plastic fitting with the internal threads of the collar cause the tip of the fitting to telescope tightly into the tapered entry to the lumen of the plastic fitting. Thus, the prior art plastic fitting can achieve a secure mechanical connection with a collar and a fluid-tight connection with the distal tip of the fitting. The extreme distal tip of the plastic fitting terminates in a single axially aligned egress port with a diameter similar to the diameter of the lumen. Thus, the distal end of the plastic fitting is not beveled to a sharp point. Plastic fittings of this type are sold by Baxter and Becton Dickinson under the trademark INTERLINK®.

Plastic fittings have been used for a variety of medical purposes, including the injection of drugs into the fitting of an IV line. The plastic fittings, however, typically have not been used for phlebotomy or during any diagnostic procedures conducted after a sample of fluid has been collected.

Sharply pointed metallic needle cannulas have many essential uses in medical practice. However, a sharply pointed metallic needle cannula creates the potential for accidental sticks. Thus, sharply pointed metallic needle cannulas are avoided whenever practical. Plastic cannulas are a suitable substitute for sharply pointed metallic cannulas in many situations, including those situations where a cannula must pierce a septum. The prior art plastic cannula is unitarily molded from plastic and includes a proximal end, a distal end and a lumen extending between the ends. The lumen is widely open and tapered at the proximal end of the plastic cannula and is configured for fluid-tight frictional engagement over the tapered tip of a typical fitting. The proximal end of a plastic cannula may further include a pair of diametrically opposite lugs that are dimensioned and configured for engagement with the threads of a collar.

The distal end of the prior art plastic cannula includes a narrow cylindrical wall that surrounds the lumen through the cannula. The narrow cylindrical wall is conically tapered to a point that is sufficiently sharp to pierce a rubber septum. In this regard, the sharpness of the distal tip normally would be limited by the diameter of the lumen through the cannula. This would result in a fairly blunt tip that might not be able to pierce through many septums. However, plastic cannulas have been developed with diametrically opposite triangular extension of the tubular sidewall that converge at the extreme distal end of the plastic cannula. These converging triangular extensions meet at a well defined point at the extreme distal end of the plastic cannula. A pair of identical side ports open transversely at the distal end and at locations between these triangular extensions. A plastic cannula of this type often is used to deliver a drug intravenously through the septum on the above-described fitting. Although the plastic cannula is sufficiently sharp to pierce a septum, it will not accidentally stick a patient.

SUMMARY OF THE INVENTION

The subject invention is directed to a kit or system of parts for efficiently delivering a specimen of blood or other bodily fluid to a portable clinical analyzer of a point-of-care testing system. The kit of the subject invention comprises a point-of-care testing cartridge. The testing cartridge may be of any of the above-described prior art testing cartridges or any yet to be developed testing cartridges that have an internal reservoir for receiving a sample of blood and an entry port that communicates with the internal reservoir of the testing cartridge. The testing cartridge may further include contact pads and sensors for communicating with a portable clinical analyzer that is capable of performing tests on a sample of blood deposited in the reservoir of the testing cartridge.

The kit may include a plastic fitting, such as the INTERLINK® fitting marketed by Baxter and Becton Dickinson. The plastic fitting includes opposed proximal and distal ends and a lumen extending therebetween. The proximal end of the plastic fitting includes a tapered entry to the lumen through the fitting that is dimensioned for fluid-tight engagement over the tapered tip of the syringe. The proximal end of the plastic fitting may further include a pair of lugs for threaded engagement with a collar. The cylindrical walls at the distal end of the plastic fitting include a slight conical taper with a blunt end equal in diameter to the diameter of the lumen. Thus, the outside diameter at the distal end of the plastic fitting is only slightly greater than the inside diameter of the lumen into the distal end of the plastic fitting, and is smaller than the outside diameter of the tip of the syringe body.

As an alternative to the above-described plastic fitting, the kit of the subject invention may include a unitarily molded plastic cannula. The plastic cannula includes a proximal end, a distal end and a lumen extending between the ends. The proximal end of the plastic cannula is identical to the proximal end of the plastic fitting. The distal end of the prior art plastic cannula includes a narrow cylindrical wall that surrounds the lumen through the cannula. The extreme distal end of the plastic cannula includes diametrically opposite triangular extensions of the tubular sidewall that converge toward one another and meet at the extreme distal end to define a point that is sufficiently sharp to pierce a rubber septum. A pair of side ports open transversely at the distal end of the plastic cannula and between the converging triangular extensions.

The kit or system of parts may comprise a syringe assembly for receiving and transferring a specimen of blood. The syringe assembly includes a syringe body with opposed proximal and distal ends. A barrel extends from the proximal end toward the distal end. The barrel includes a wide opening at the distal end of the syringe body and a fluid receiving chamber that extends distally from the wide opening. The syringe body further includes a tapered tip that extends from the distal end to the barrel. The tip is provided with a small-diameter passage that extends from the extreme distal end into communication with the fluid receiving chamber in the barrel. The syringe body may further include a collar that extends distally from the chamber and concentrically around the tip. The collar includes an array of internal threads. A plunger is disposed in the open proximal end of the barrel and is slidably movable in the fluid receiving chamber.

The present invention also is directed to a method for efficiently delivering a specimen of blood or other bodily fluid to a point-of-care testing cartridge with a syringe comprising a plastic fitting, such as the above-described INTERLINK® fitting marketed by Baxter and Becton Dickinson. The method includes obtaining a specimen of fluid with the syringe.

This step may include obtaining the specimen with or without the plastic fitting mounted on the syringe. For example, the fitting of an IV system can be placed in communication with the tip of the syringe so that the syringe and the IV system both can be in communication with the patient and the source of blood or other bodily fluid in the patient. Alternatively, a needle assembly can be mounted to the tip of the syringe, and the distal end of the needle cannula can be placed in communication with a blood vessel. The plunger of the syringe assembly then may be moved proximally to draw a selected volume of fluid into the fluid receiving chamber of the syringe body. The method then continues by separating the syringe assembly from the fitting, the needle assembly or other accessing means. In those situations where the specimen is obtained without the plastic fitting then the method proceeds by mounting the plastic fitting on the syringe after the specimen has been obtained.

The method proceeds by placing the distal tip of the plastic fitting in communication with the inlet port of the testing cartridge. The narrow distal end of the plastic fitting can be aimed easily into the entry port of the testing cartridge.

The method concludes by slidably moving the plunger of the syringe assembly in a distal direction relative to the syringe body for urging a selected quantity of fluid from the chamber of the syringe body into the reservoir of the testing cartridge. The syringe body and the plastic fitting then are separated from the testing cartridge and discarded in a safe conventional manner. The entry port of the testing cartridge then is closed and the contact pads and sensors of the testing cartridge then are placed in communication with the sensing device for performing a selected battery of tests on the sample of fluid in the reservoir of the testing cartridge.

An alternate method in accordance with the subject invention comprises a step of providing the above-described plastic cannula in place of the plastic fitting. The method of the subject invention then employs the above described syringe assembly and the plastic cannula to obtain a sample of the fluid.

The method proceeds by providing the above-described point-of-care testing cartridge and placing the distal tip of the plastic cannula in communication with the inlet port of the testing cartridge. The narrow distal end of the plastic cannula can be aimed easily to the entry port of the testing cartridge. Additionally, the symmetrically tapered walls at the distal tip of the plastic cannula can be telescoped into engagement with tapered entry port of the testing cartridge.

The method concludes by slidably moving the plunger of the syringe assembly in a distal direction relative to the syringe body for urging a selected quantity of fluid from the chamber of the syringe body into the reservoir of the testing cartridge substantially as in the above-described first optional method of the subject invention. Alternatively, the testing cartridge may be placed in communication with the sensing device prior to urging the fluid into the testing cartridge.

The method of the present invention reduces the volumetric flow rate of the sample as it leaves the plastic fitting and enters the testing cartridge due to the reduction in the cross-sectional area of the distal end of the plastic fitting relative to the cross sectional area of the distal end of the syringe.

Another attribute of the present invention is that the plastic fitting may be positioned by the user at the inlet port of the testing cartridge at a variety of different entry angles relative to the cartridge because the plastic fitting facilitates the venting of any air from within either the tip of the syringe or from within the plastic fitting, before or during the transfer of the specimen into the cartridge. This is a significant advantage and improvement over the use of a syringe without any fitting whereby the syringe tip would have to be held at about 45 degrees relative to the cartridge because if the syringe is held at 90 degrees relative to the cartridge, an air-tight seal is created between the syringe and the cartridge which in turn prevents adequate venting of trapped air, which in turn makes it difficult for the use to transfer the correct specimen volume.

DETAILED DESCRIPTION

Figure 1:
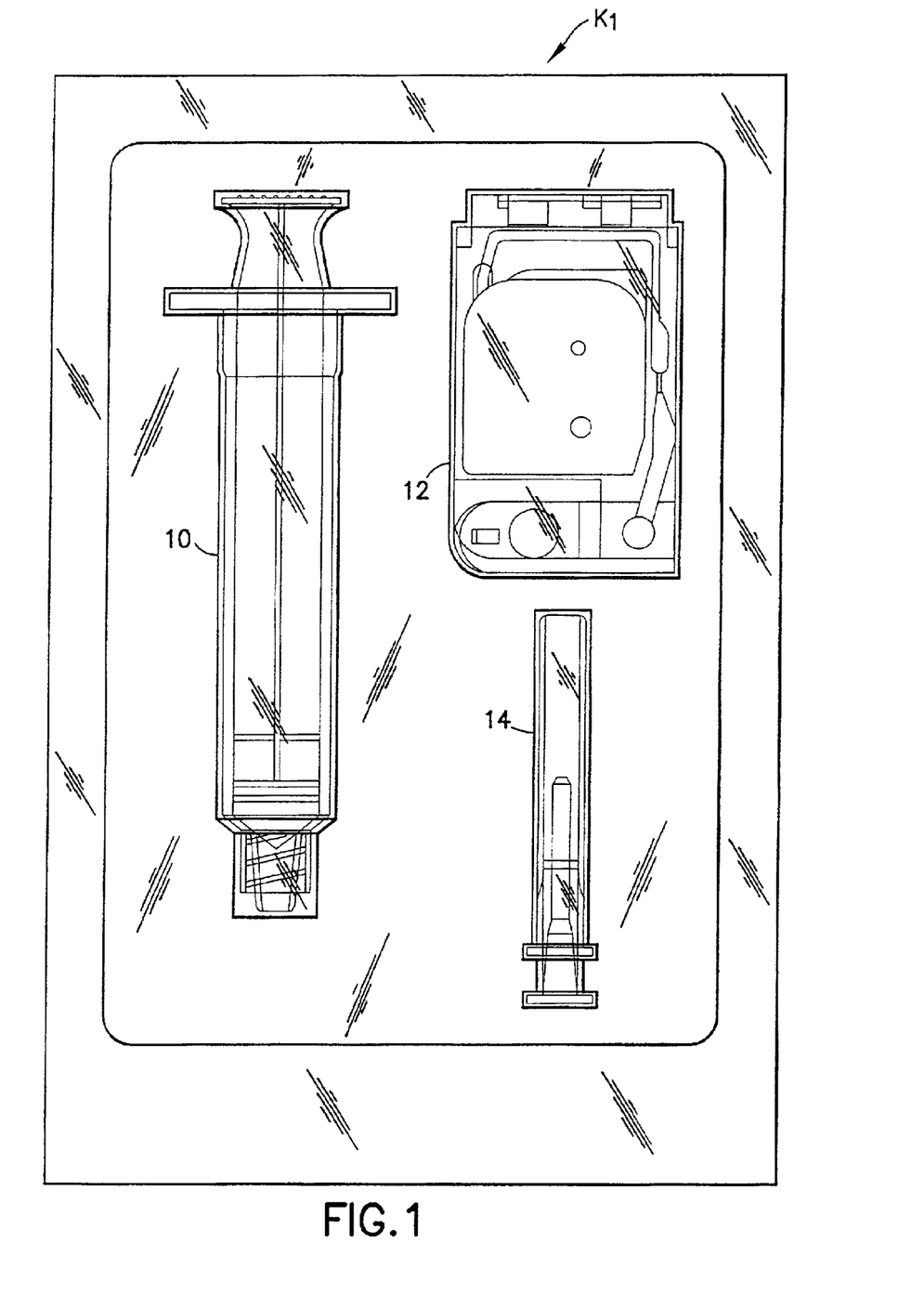
FIG. 1 is a top plan view of a first embodiment of a kit in accordance with the subject invention.
Figure 4:
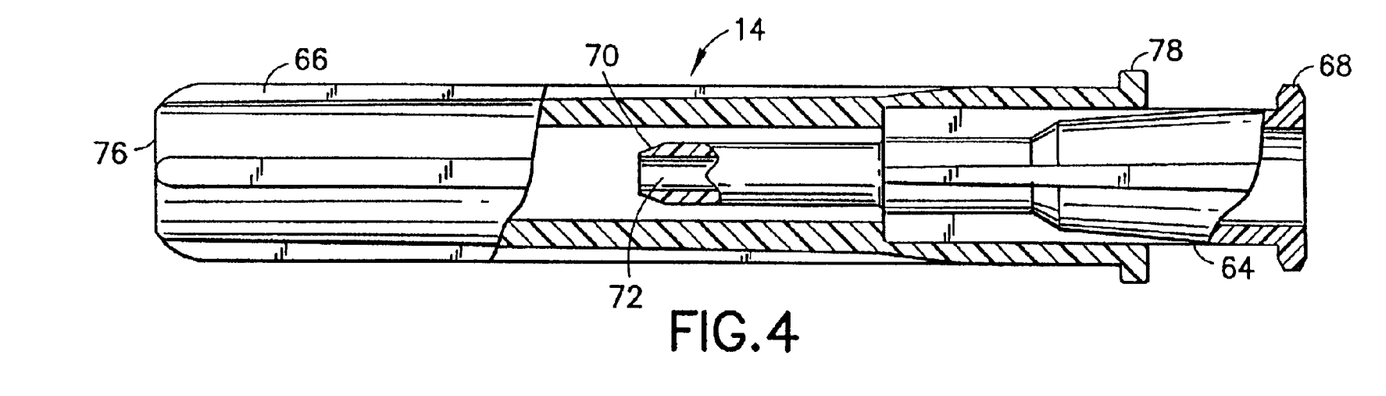
FIG. 4 is a side elevational view of a plastic fitting assembly of the kit of FIG. 1.

A kit in accordance with a first embodiment of the subject invention is identified generally by the reference $K_1$ in FIG. 1. Kit $K_1$ includes a syringe assembly 10, as shown more clearly in FIG. 2, a point-of-care testing cartridge 12, and a plastic fitting assembly 14 as shown in FIG. 4.

Figure 2:
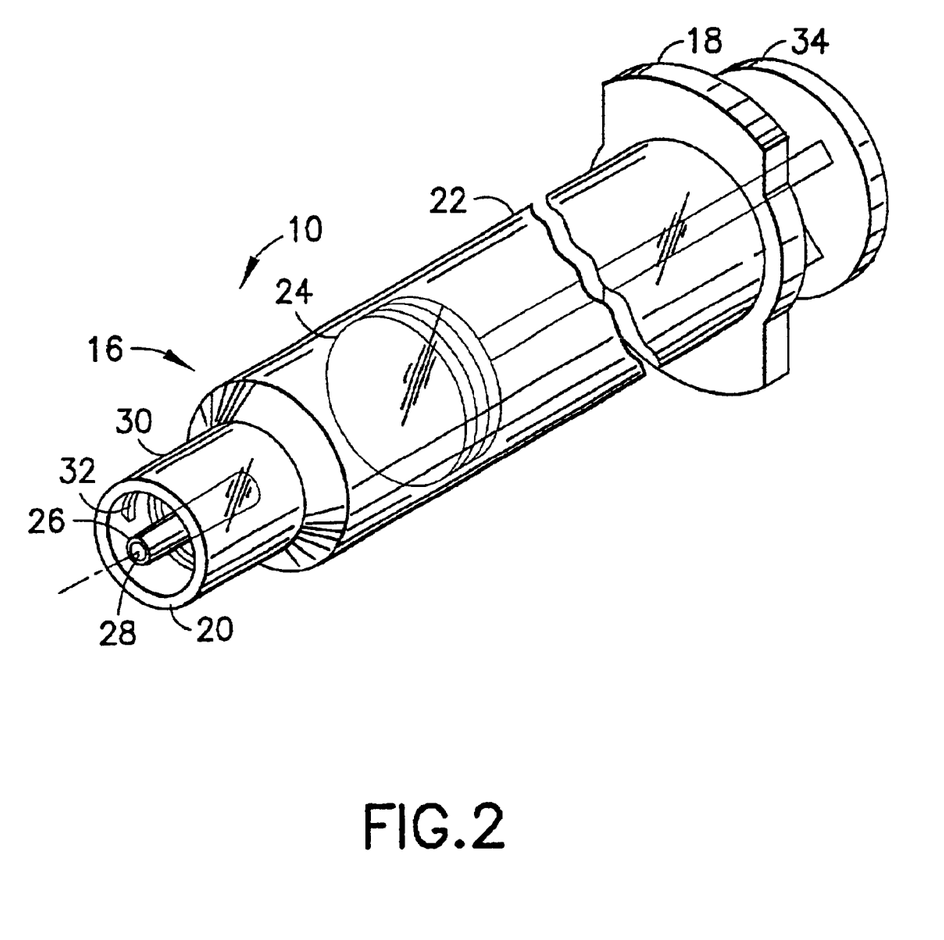
FIG. 2 is a perspective view of a syringe assembly from the kit of FIG. 1.

Syringe assembly 10, as shown in FIG. 2, includes a syringe body 16 having a proximal end 18 and a distal end 20. A barrel 22 extends distally from proximal end 18 and defines a cylindrical fluid receiving chamber 24 that is widely open at proximal end 18. A frustoconically tapered tip 26 extends from barrel 22 to distal end 20 of syringe body 16. Tip 26 is provided with a narrow cylindrical passage 28 that communicates with fluid receiving chamber 24 of barrel 22. A collar 30 projects distally from barrel 22 and concentrically surrounds tip 26. Collar 30 is provided with an internal array of threads 32. Syringe assembly 10 further includes a plunger 34 slidably disposed in fluid receiving chamber 24 and in fluid-tight engagement with the cylindrical walls of chamber 22. Plunger 34 can be moved alternately in proximal or distal directions for urging fluid through passage 28 in tip 26 and into or out of fluid receiving chamber 24.

Figure 3:
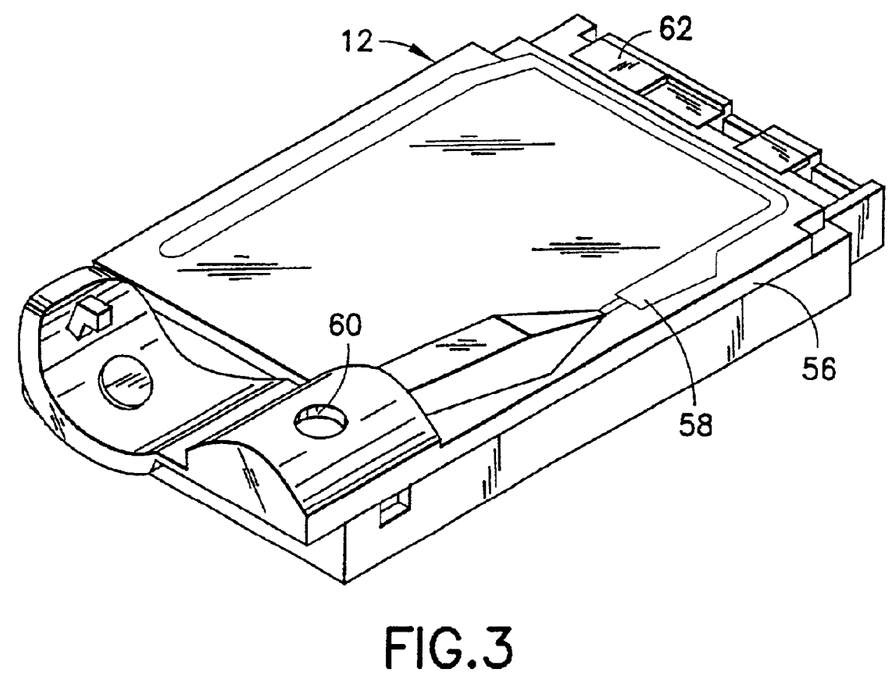
FIG. 3 is a perspective view of the point-of-care testing cartridge of the kit shown in FIG. 1.

Point-of-care testing cartridge 12 of kit $K_1$ is shown in FIG. 3 and may be of any of several prior art designs, including those manufactured by i-STAT Corporation, Diametrics Medical, Inc., AVL Scientific Corporation or any other such testing cartridges that are available or become available. One such testing cartridge is disclosed in U.S. Pat. No. 5,638,828, the disclosure of which is incorporated herein by reference.

Testing cartridge 12 includes a generally rectangular body 56 with a length of approximately 1.5–2.0", a width of about 1.0" and a thickness of about 0.25". A fluid reservoir 58 is formed inside body 56 of cartridge 12 and has a volume in the range of 65 $\mu$l and 110 $\mu$l. Body 56 further includes an entry port 60 that communicates with reservoir 58. Entry port 60 is slightly tapered from a relatively large diameter portion externally on housing 56 to a relatively smaller cross-section closer to reservoir 58. Testing cartridge 12 further includes contact pads and sensors 62 that can be placed in communication with a portable clinical analyzer for performing various point-of-care diagnostic tests on the sample of blood in the reservoir 58 and for providing various readout data that can be used by a health care technician at the point-of-care and/or at a remote location.

Fitting assembly 14 of kit $K_1$ is shown more clearly in FIG. 4 and includes a plastic fitting 64 and a plastic safety shield 66. Plastic fitting 64 may be of the type sold by Baxter under the trademark INTERLINK®. As shown more clearly in FIG. 5, the fitting 64 is unitarily molded from a plastic material and includes a proximal end 68 and, a distal end 70 to define a length of slightly over 1.0". A lumen 72 extends between ends 68 and 70. Portions of lumen 72 adjacent proximal end 68 define a tapered entry that substantially conforms to the size and shape of the tapered passage in hub 46 of needle assembly 36. Thus, the tapered entry to lumen 72 at proximal end 68 of fitting 64 can provide a fluid-tight frictional engagement with tapered tip 26 of syringe body 16. Portions of lumen 72 adjacent proximal end 68 define a maximum inside diameter of approximately 0.169". Proximal end 68 of fitting 64 is characterized further by a pair of diametrically opposite projections 74 that are dimensioned and configured for engagement with internal threads 32 of collar 30. Thus, projections can be engaged threadedly with collar 30 for urging the tapered proximal open end of lumen 72 into fluid-tight frictional engagement with tapered distal tip 26 of syringe body 16. In other embodiments, the syringe may not have a collar, and fitting 64 can merely be moved axially into fluid-tight frictional engagement over distal tip 26.

Figure 5:
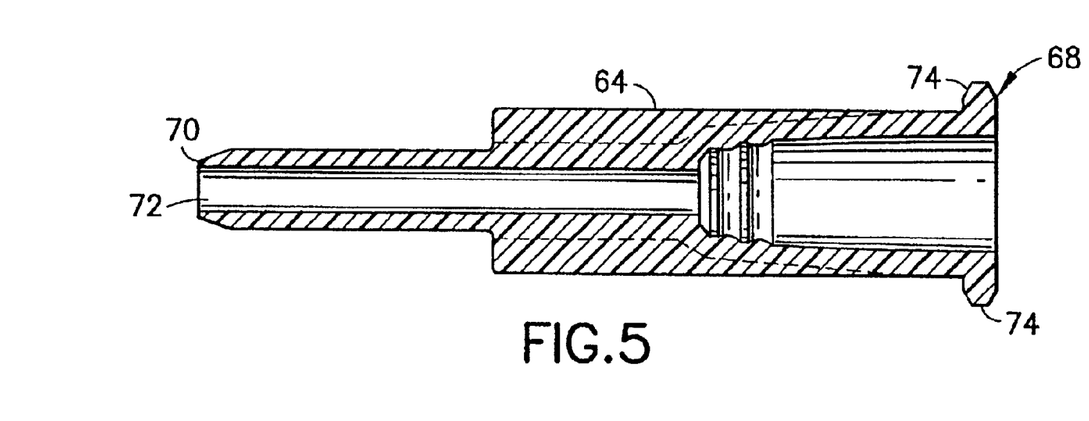
FIG. 5 is a longitudinal cross-sectional view of the plastic fitting shown in FIG. 4.

Portions of fitting 64 adjacent distal end 70 define a frustoconical taper having a minimum outside diameter of approximately 0.072" at distal end 70 to a maximum outside diameter 0.10" at a location spaced from distal end 70 by a distance of about 0.045". Plastic fitting 64 continues at a substantially constant outside diameter of approximately 0.10" to a location spaced approximately 0.40" from distal end 70. Both the minimum outside diameter at distal end 70 and the maximum outside diameter of 0.10" at locations adjacent the frustoconical taper are substantially less than corresponding dimensions of distal tip 26 of syringe body 16. Furthermore, the degree of taper at distal end 70 of fitting 64 is greater than the taper existing on tip 26 of syringe body 16.

Returning to FIG. 4, safety shield 66 of fitting assembly 14 includes a closed distal end 76 and an open proximal end 78. Proximal end 78 of safety shield 66 can be telescoped over distal end 70 of fitting 64 and can be engaged frictionally with portions of blunt plastic cannula 64 between proximal and distal ends 68 and 70.

Kit $K_1$ of FIG. 1 is employed initially by accessing syringe assembly and obtaining a specimen of bodily fluid from a patient. In this regard, syringe assembly can be used with a conventional needle assembly or by direct connection of Luer tip 26 with a fitting of an IV access system. Still further, the specimen of bodily fluid can be obtained by first mounting fitting 64 to Luer tip 26 of syringe assembly.

After a sufficient volume of fluid has been drawn into fluid receiving chamber 24, syringe assembly 10 is moved away from the patient or away from any other source of the fluid specimen (e.g., an IV access system). Any needle cannula that may have been used to obtain the specimen then is separated from syringe body 16 to leave syringe assembly 10 in the condition shown in FIGS. 1 and 2. For example, a syringe body that has no collar may be employed with a sharps receptacle that has a tapered opening. A needle assembly that may have been used to obtain the fluid specimen and distal end portions of the syringe body may be inserted into the tapered opening of the sharps receptacle, and may be translated in the opening sufficiently for tapered portions of the opening to engage proximally of the needle hub. A proximal pulling force on the syringe body then will separate the needle assembly from the syringe tip and will permit the used needle assembly to fall safely into the sharps receptacle. In other situations, a device may be provided for unthreading a needle assembly from collar 30. The unthreading device may merely grip outer circumferential portions of the needle hub, and syringe body 16 may be rotated relative to needle assembly. Other devices for separating a used needle assembly from syringe body 16 are known to those skilled in this art.

Figures 6, 7:
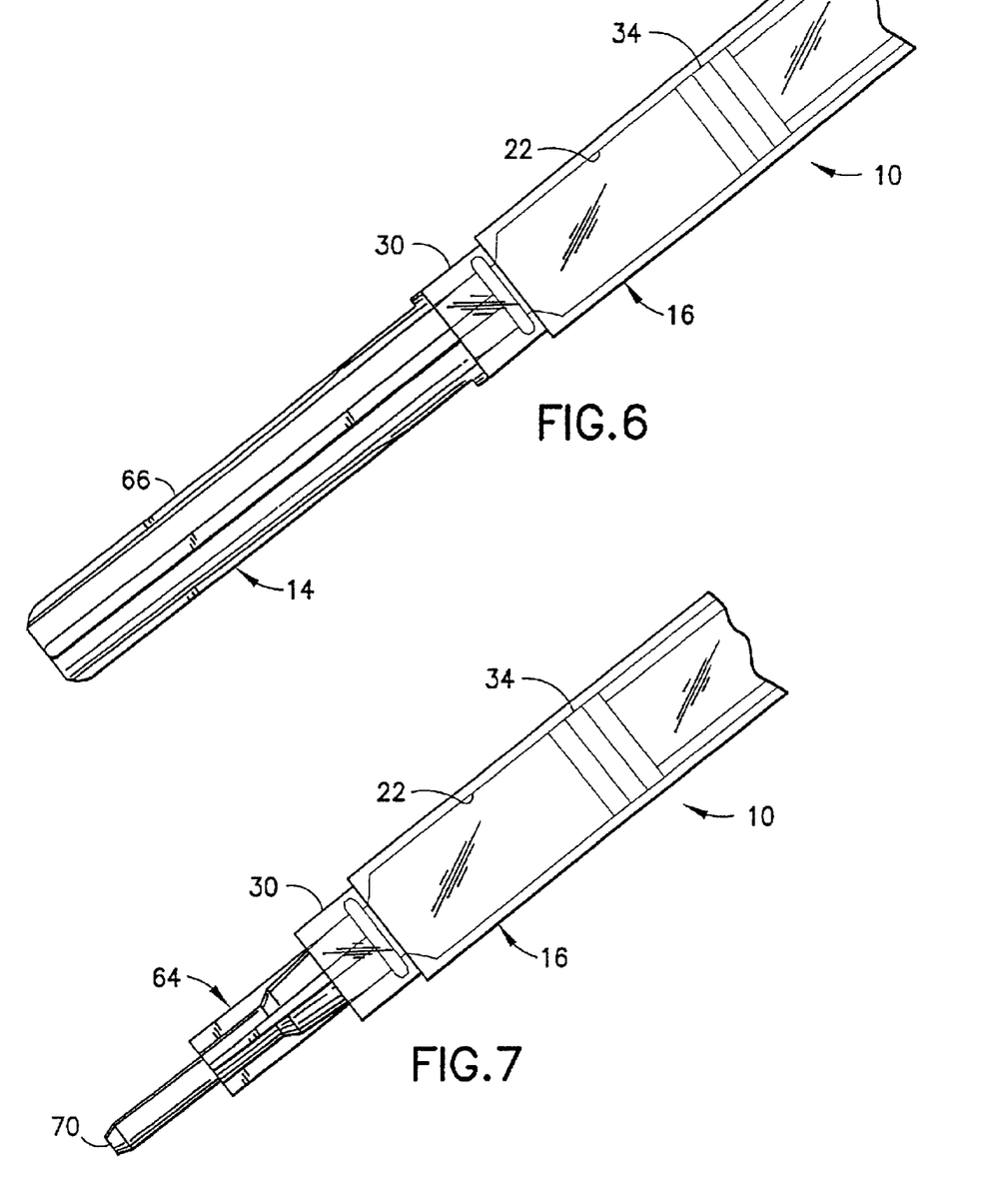
FIG. 6 is a side elevational view of the plastic fitting and safety shield mounted to the distal end of the syringe.
FIG. 7 is a side elevational view similar to FIG. 6, but showing the protective cap removed from the plastic fitting.
Figure 8:
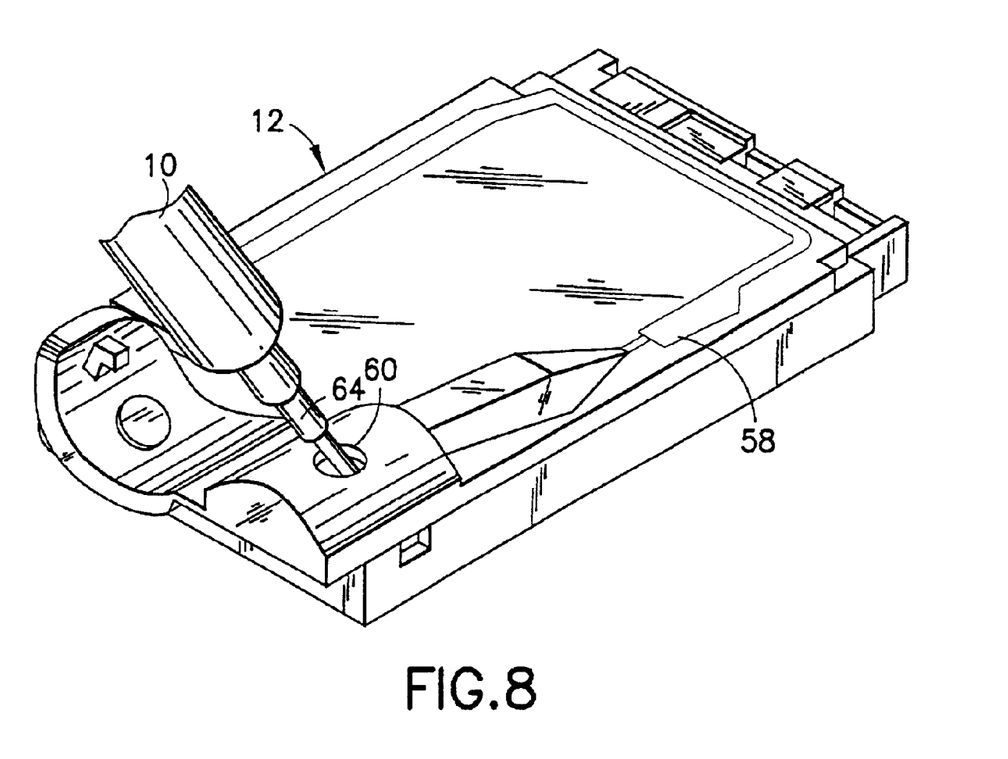
FIG. 8 is a perspective view showing the syringe assembly and plastic fitting placed in communication with the entry port of the point-of-care testing cartridge of the kit.
Figure 9:
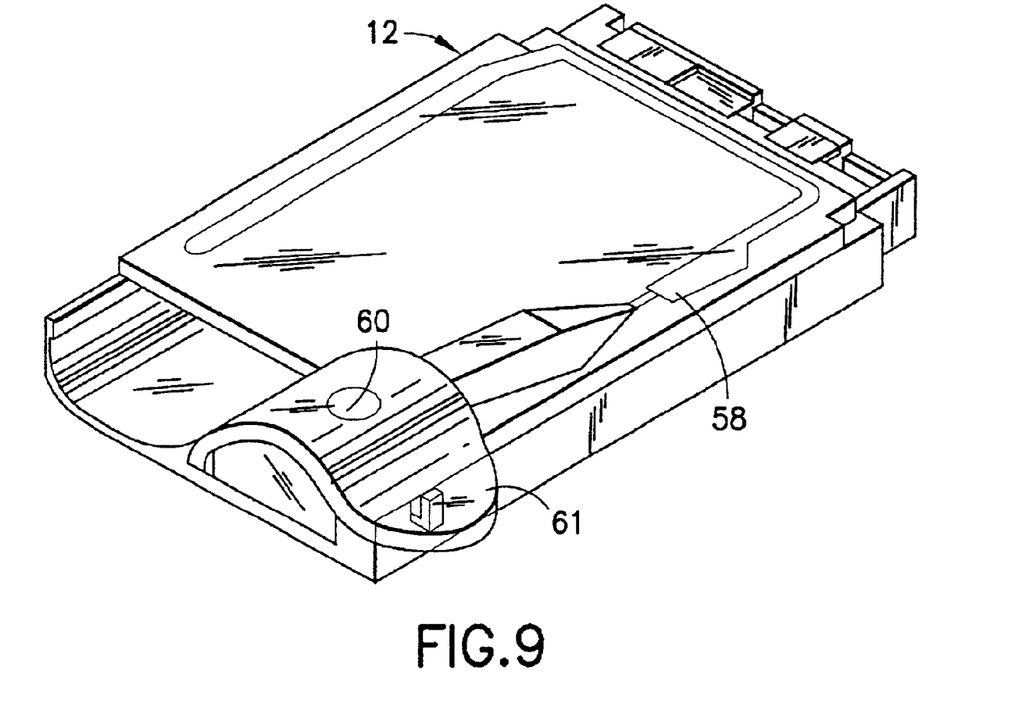
FIG. 9 is a perspective view of the point-of-care testing cartridge after separation of the syringe assembly and plastic fitting and after closing of the entry port.

Fitting assembly 14 then is engaged with distal end 20 of syringe body 16, as shown in FIG. 6. This engagement may involve the mere axial movement of proximal end 68 of fitting 64 over tapered distal tip 26 of syringe body 16 for those instances where syringe body 16 has no collar. In these situations, a fluid-tight frictional interfit is achieved between the tapered proximal entry to lumen 72 and the tapered outer surface of tip 26. In other embodiments, lugs 74 of fitting 64 may merely be rotated into engagement with internal threads 32 of collar 30 on syringe body 16. In both embodiments, lumen 72 of fitting 64 is placed in fluid communication with passage 28 of tip 26, and hence in communication with fluid receiving chamber 24 of syringe body 16. Cap 66 of fitting assembly 14 then is separated from fitting 64 to expose tapered distal end 70 of fitting 64, as shown in FIG. 7.

Figure 10:
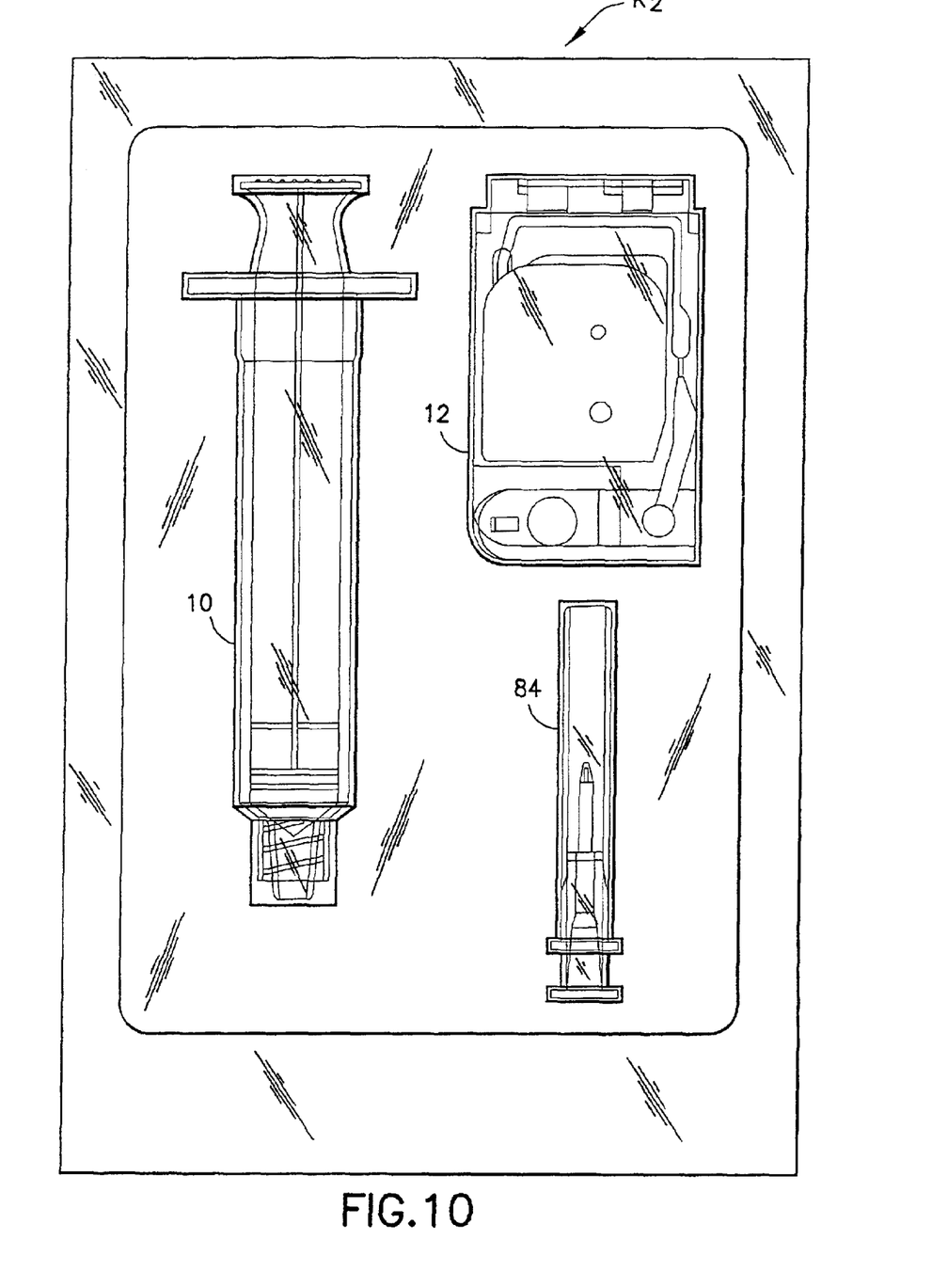
FIG. 10 is a top plan view of a second embodiment of a kit in accordance with the subject invention.

Kit $K_1$ of the subject invention then is used by placing narrow conically tapered distal tip 70 of fitting 64 into tapered entry port 60 of point-of-care testing cartridge 12, as shown in FIG. 10. A selected volume of fluid is transferred from fluid receiving chamber 24 of syringe body 16 to reservoir 58 of testing cartridge 12 by urging plunger 34 of syringe assembly 10 distally relative to syringe body 16. Thus, fluid is urged from fluid receiving chamber 24 through passage 28 in tip 26, through lumen 72 of fitting 64 and into entry port 60. The narrow tapered configuration of portions of fitting 64 adjacent distal end 70 facilitates alignment of syringe assembly 10 with entry port 60 of testing cartridge 12 and further facilitates fluid communication between syringe assembly 10 and testing cartridge 12.

Figure 11:
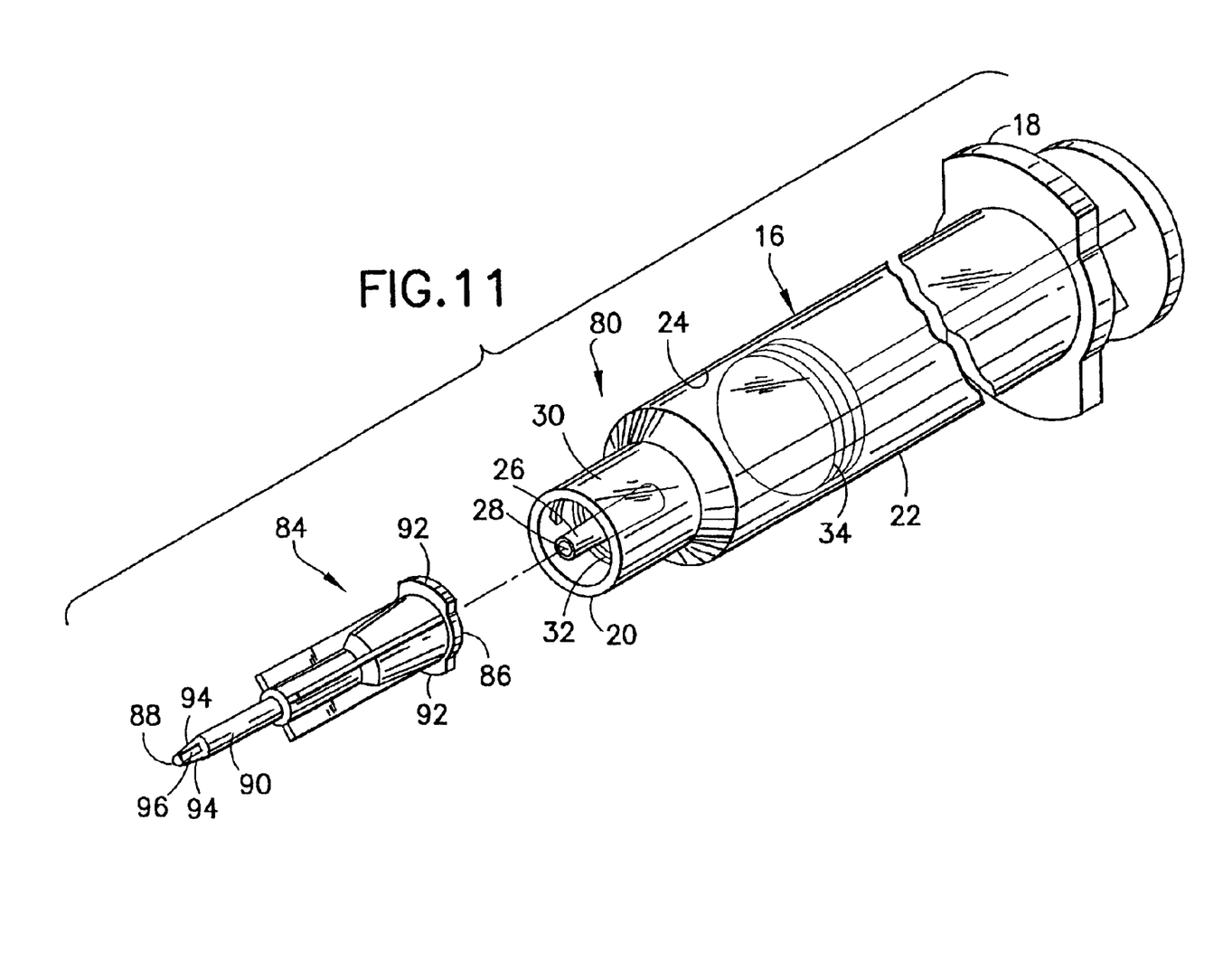
FIG. 11 is an exploded perspective view of a syringe assembly and needle assembly from the kit of FIG. 12.
Figure 12:
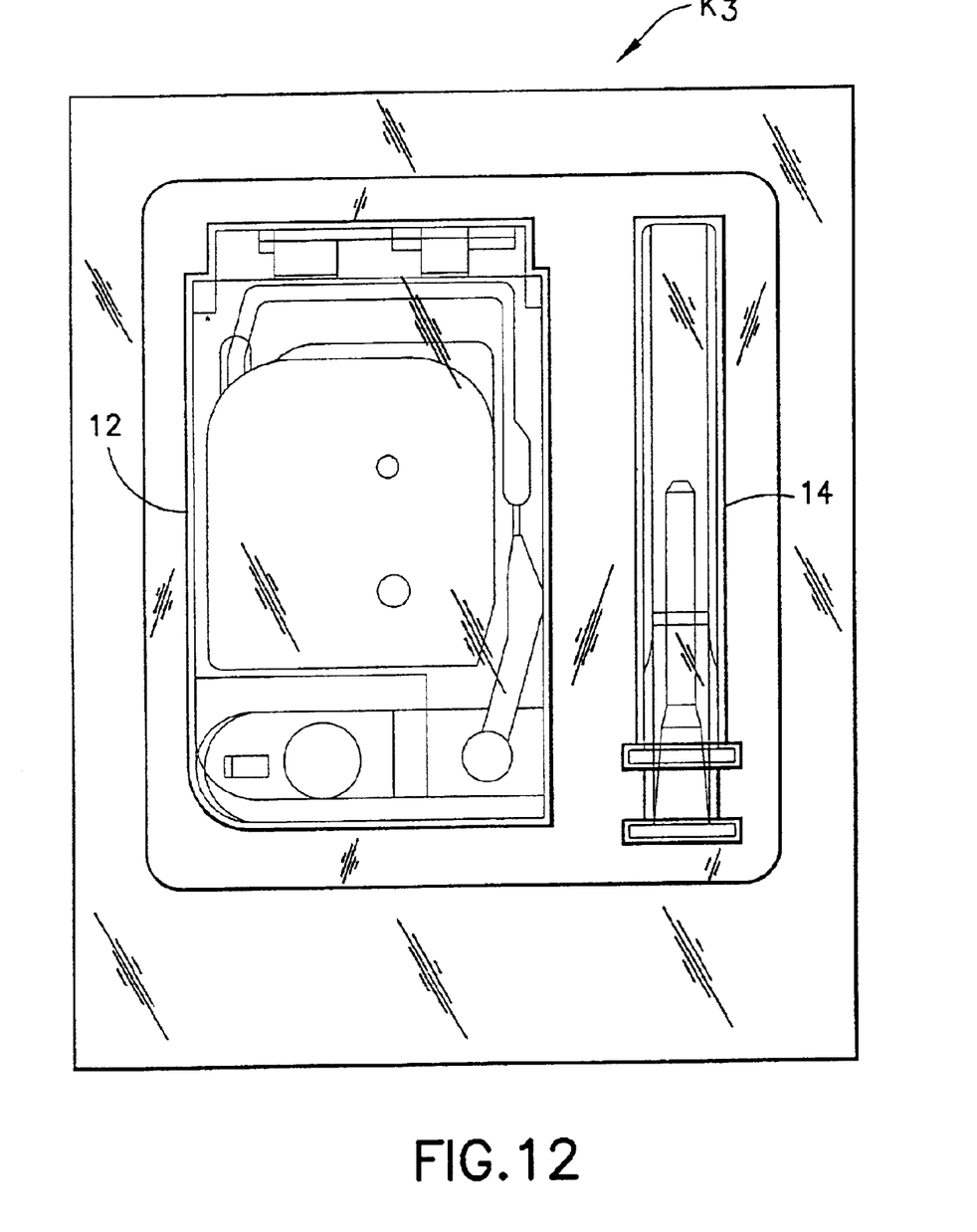
FIG. 12 is a top plan view of a third embodiment of a kit in accordance with the subject invention.
Figure 13:
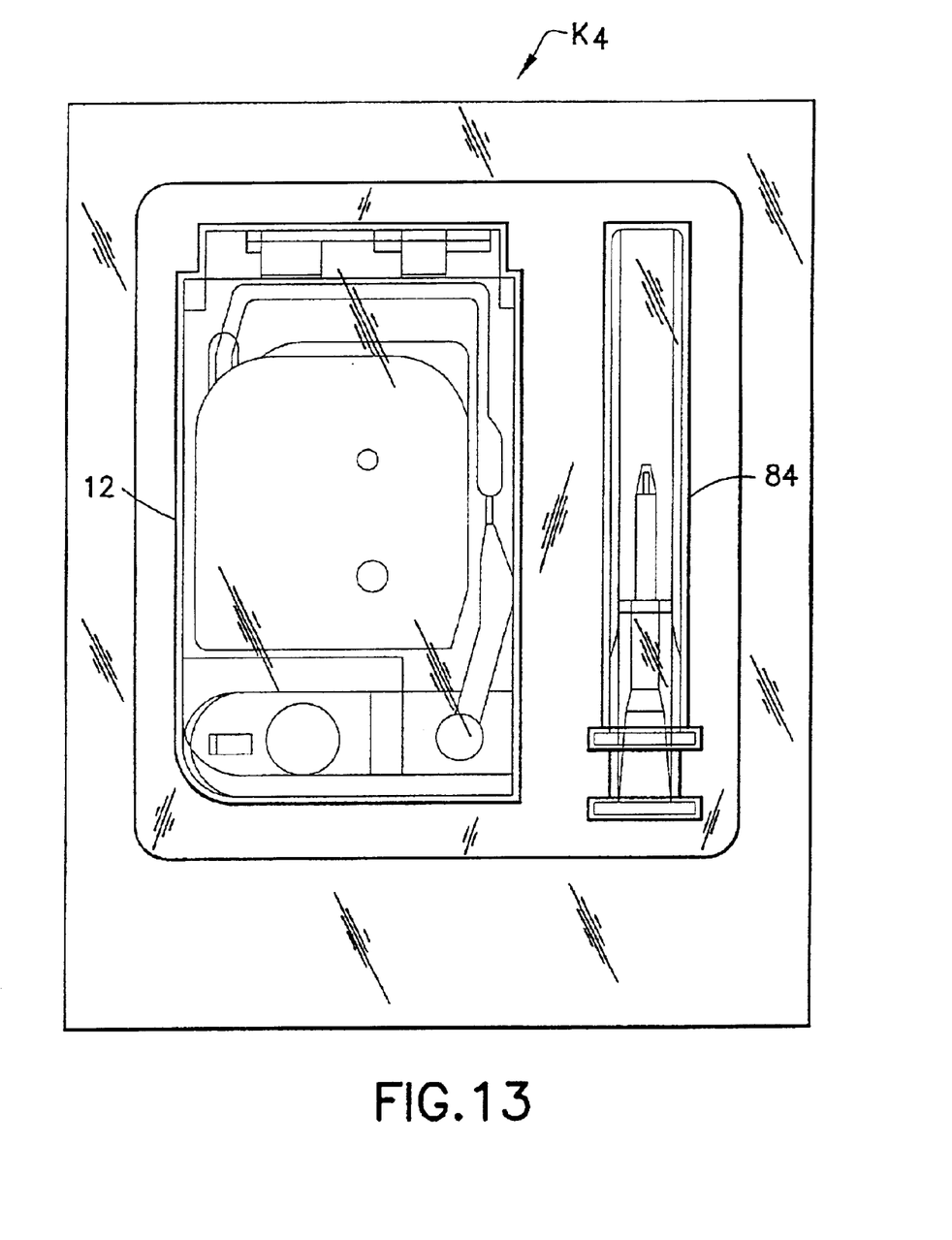
FIG. 13 is a top plan view of a fourth embodiment of a kit in accordance with the subject invention.

After a sufficient volume of fluid has been deposited into reservoir 58 of testing cartridge 12, syringe assembly 10 is separated from testing cartridge 12 and discarded. Cover 61 of testing cartridge 12 then is rotated over entry port 60, as shown in FIG. 11, and contact pads and sensors 62 of testing cartridge 12 are placed in communication with the portable clinical analyzer for performing selected diagnostic tests on blood in reservoir 58.

An alternate kit in accordance with the subject invention is identified by the reference $K_2$ in FIG. 10. Kit $K_2$ employs a syringe assembly 10 that is identical to syringe assembly 10 of FIG. 2. Kit $K_2$ further includes a testing cartridge 12 identical to the testing cartridge of FIG. 3 and a blunt plastic cannula 84, as shown in FIGS. 10 and 11.

Plastic cannula 84 has a proximal end 86, a distal end 88 and a lumen 90 extending between the ends. Portions of lumen 90 adjacent proximal end 86 define a taper that substantially matches tapered distal tip 26 on syringe body 16. Thus, tapered tip 26 of syringe body 16 can be placed in fluid-tight engagement with the proximal end of lumen 90 in plastic cannula 84. Proximal end 86 of plastic cannula 84 is further characterized by a pair of diametrically opposite lugs 92 that are dimensioned and configured for engagement with threads 32 of collar 30. Thus, lumen 90 through plastic cannula 84 can be placed in communication with passage 28 in tip 26 and fluid receiving chamber 24 of syringe body 16. Distal end 88 of plastic cannula 84 includes a pair of converging diametrically opposite triangular portions that meet at a well defined conical tip. The triangular projections are separated from one another and two oppositely facing ports are defined between the triangular projections.

Kit $K_2$ of FIG. 10 is used substantially the same as kit $K_1$. More particularly, a specimen of blood or other bodily fluid is obtained with syringe 10 substantially as described above. Plastic cannula 84 may be used to obtain the specimen. However, if the specimen was obtained without plastic cannula 84, plastic cannula 84 then is mounted to syringe 10 after obtaining the specimen by placing proximal end 86 over Luer tip 26. A selected volume of fluid is transferred from fluid receiving chamber 24 of syringe body to reservoir 58 of testing cartridge 12 by urging plunger 34 of syringe assembly 10 distally relative to syringe body 16. Thus, fluid is urged from fluid receiving chamber 24 through passage 28 in tip 26, through lumen 90 of plastic cannula 84 and into entry port 60. The conically pointed distal end 88 of plastic cannula 84 facilitates alignment of syringe assembly 10 with entry port 60 of testing cartridge 12 and further facilitates fluid communication between syringe assembly 10 and testing cartridge 12.

After a sufficient volume of fluid has been deposited into reservoir 58 of testing cartridge 12, needle assembly 10 is separated from testing cartridge 12 and discarded. Cover 61 of testing cartridge 12 then is rotated over entry port 60, as shown in FIG. 19 above. Contact pads and sensors 62 of testing cartridge 12 are placed in communication with the portable clinical analyzer for performing selected diagnostic tests on the fluid in reservoir 58.

What is claimed is:

1. A kit for obtaining a sample of fluid from a patient and enabling point-of-care testing of said sample of fluid, said kit comprising:

a syringe assembly for selectively drawing and expelling a sample of fluid, the syringe assembly including a distal end, a tip projecting at said distal end and having a passage communicating with a fluid receiving chamber of said syringe, said tip having selected outside cross-sectional dimensions;

a point-of-care testing cartridge having an internal reservoir and an inlet port, the inlet port having cross-sectional dimensions configured for receiving the tip of the syringe; and a fitting having a proximal end configured for removable communication with the tip of said syringe, a distal end tapered to outside cross-sectional dimensions sufficiently smaller than the outside cross-sectional dimensions of the tip of the syringe for permitting removable communication in said entry port of said testing cartridge and venting of air from said entry port for delivering said sample of said fluid from said syringe to said reservoir of said testing cartridge.

2. A kit for obtaining a sample of fluid from a patient and enabling point-of-care testing of said sample of fluid, said kit comprising:

a syringe assembly for selectively drawing and expelling a sample of fluid, said syringe assembly having a distal end, a tip projecting at said distal end;

a point-of-care testing cartridge having an internal reservoir and an inlet port; and a fitting having a proximal end configured for removable mounting to said tip of said syringe, a distal end configured for removable communication with said entry port of said testing cartridge and a lumen extending between the ends for delivering said sample of said fluid from said syringe to said reservoir of said testing cartridge, said distal end of said fitting comprises a pair of converging triangular portions meeting at said distal end and separated from one another by transverse ports communicating with said lumen through said fitting.

3. A kit for use with a syringe to obtain a sample of fluid from a patient and to enable point-of-care testing of said sample of fluid, said kit comprising:

a point-of-care testing cartridge having an internal reservoir and an inlet port; and a fitting having a proximal end configured for removable communication with said syringe, a distal end configured for removable communication with said entry port of said testing cartridge and a lumen extending between said ends for delivering said sample of said fluid from said syringe to said reservoir of said testing cartridge, said distal end of said fitting comprising a pair of converging triangular portions meeting at said distal end and separated from one another by transverse ports communicating with said lumen through said fitting.

4. A method for delivering a sample of fluid to a testing cartridge of a point-of-care blood testing system, said testing cartridge including an internal reservoir for retaining a sample of fluid and an entry port extending from an external location on said testing cartridge into communication with said reservoir, said entry port having selected cross-sectional dimensions, said method comprising:

employing a syringe to obtain a sample of fluid;

providing a plastic fitting having a proximal end configured for mating with said syringe, a narrow tapered distal end and a lumen extending between said ends of said plastic fitting, said narrow tapered distal end of said plastic fitting having outside cross-sectional dimensions smaller than said cross-sectional dimensions of said entry port;

mounting said proximal end of said plastic fitting to said syringe such that said lumen through said plastic fitting can be placed in communication with said fluid in said syringe;

placing said narrow tapered distal end of said plastic fitting into said entry port of said testing cartridge so that at least portions of said narrow tapered distal end are spaced from inner peripheral portions of said entry port to define space for venting of air;

urging fluid from said syringe through said plastic fitting and into said reservoir of said testing cartridge while simultaneously venting air between said narrow tapered distal end of said plastic fitting and said entry port;

separating said syringe and said plastic fitting from said testing cartridge; and closing said entry port.

5. The method of claim 4, wherein said syringe includes a distal tip having a tapered outer surface and a passage extending therethrough, said proximal end of said plastic fitting having a tapered entry to said lumen, said step of mounting said proximal end of said plastic fitting to said syringe comprising placing said tip of said syringe into fluid-tight frictional engagement with said tapered entry to said lumen of said plastic fitting.

6. The method of claim 5, wherein said plastic fitting has a safety cap mounted over said distal end, said method further comprising the step of removing said safety cap from said plastic fitting after mounting said plastic fitting to said syringe and before placing said distal end of said plastic fitting into communication with said entry port of said testing cartridge.

7. The method of claim 6, wherein the syringe comprises a needle assembly mounted thereto for obtaining said sample of fluid, said method further comprising the step of separating said needle assembly from said syringe prior to mounting said plastic fitting to said syringe.

8. A method for delivering a sample of bodily fluid for testing, comprising:

providing a point-of-care testing cartridge, said testing cartridge including an internal reservoir for retaining a sample of fluid and an entry port extending from an external location on said testing cartridge into communication with said reservoir;

providing a syringe with a fluid receiving chamber;

providing a plastic cannula having a proximal end configured for mounting on said syringe, a tapered distal end and a lumen between the ends, the lumen having opposed side ports at said distal end;

drawing a sample of said fluid into said fluid receiving chamber; and employing said plastic cannula with said syringe for delivering said sample of said fluid such that said lumen communicates from said fluid receiving chamber, through said lumen and said point-of-care testing cartridge, said employing step comprising urging a selected volume of fluid from the fluid receiving chamber, through the side ports of said plastic cannula and into said entry port of said testing cartridge.

9. The method of claim 8, further comprising the steps of providing an accessing means for accessing the fluid, and placing said syringe in communication with said accessing means prior to drawing said sample.

10. The method of claim 9, further comprising the step of removing said syringe and said plastic cannula from said testing cartridge after urging the selected volume of fluid into said reservoir of said testing cartridge and disposing of said syringe and said plastic cannula.

* * * * *